United States Patent [19]

Yeboah

[11] 4,423,240

[45] Dec. 27, 1983

[54] METHODS FOR PREPARING CYCLOPOLYSILOXANE

[75] Inventor: Yaw D. Yeboah, Scotia, N.Y.

[73] Assignee: General Electric Company, Schenectady, N.Y.

[21] Appl. No.: 367,704

[22] Filed: Apr. 12, 1982

[51] Int. Cl.$^3$ .............................. C07F 7/04; C07F 7/08
[52] U.S. Cl. .................................................... 556/460
[58] Field of Search ........................................ 556/460

[56] References Cited

U.S. PATENT DOCUMENTS

| | | | |
|---|---|---|---|
| 2,769,829 | 11/1956 | Dobay | 556/460 |
| 3,398,173 | 8/1968 | Goosens | 556/460 X |
| 3,627,805 | 12/1971 | Thomas et al. | 556/460 |
| 3,846,464 | 11/1974 | Razzano | 556/460 |
| 3,983,148 | 9/1976 | Reedy et al. | 556/460 |
| 4,108,882 | 8/1978 | Mahone | 556/460 |
| 4,197,251 | 4/1980 | Hirakawa et al. | 556/460 |

Primary Examiner—Paul F. Shaver
Attorney, Agent, or Firm—Richard J. Traverso; James C. Davis, Jr.; James Magee, Jr.

[57] ABSTRACT

Cyclic polysiloxanes can be prepared by hydrolysis of dimethyldichlorosilane and water or aqueous hydrochloric acid in the presence of the anionic surfactant, sodium lauryl sulfate, to give good yields of cyclic polysiloxanes and minimal amounts of linear silanols.

5 Claims, No Drawings

METHODS FOR PREPARING CYCLOPOLYSILOXANE

BACKGROUND OF THE INVENTION

This invention relates to an improved method for hydrolyzing and condensing dimethyldichlorosilane so as to prepare a cyclic siloxane of the general formula:

$$[(CH_3)_2SiO]_m \qquad \text{I}$$

where m is a whole number predominantly ranging from 3-6, inclusive. This preparation of cyclic polysiloxanes is accomplished by hydrolyzing dimethyldichlorosilane in the presence of the anionic surfactant, sodium lauryl sulfate (hereinafter identified as "sulfate") having the formula $$CH_3(CH_2)_{11}-O-\underset{\underset{O}{\|}}{\overset{\overset{O}{\|}}{S}}-ONa \qquad \text{II}$$

By means of this invention, the dimethyldichlorosilane when hydrolyzed gives a number of cyclic polysiloxanes according to formula I which predominantly are of the type where m is 3-6 with a minimum of linear dimethylsiloxanes terminated with silanol groups.

Cyclic polysiloxanes, particularly cyclic dimethyl siloxanes, such as those in formula I where m is 4 (also called "tetramer") or m is 5 (also called "pentamer"), or even where m is 6 (also called "hexamer") are extremely desirable in the silicone art. Even the lowest cyclic polysiloxane where m is 3 (also called "trimer") has a value, but is usually formed in smaller amounts than either the tetramer or the pentamer.

These cyclic dimethylsiloxanes have many uses. From these cyclic polysiloxanes there may be prepared silicone rubbers, silicone fluids, including silicone lubricating oils, etc. These cyclics can be used by themselves for foam suppression in certain applications.

It is commercially important that in preparing these polysiloxanes that they be in a cyclic form since, from a purity viewpoint when making silicone gums the cyclics are the starting materials used with alkali metal hydroxides as condensing agents. Thus, the silicone gums are generally prepared by heating the cyclic tetramer with KOH to form the gum which in turn is filled with reinforcing fillers, such as fume silica, and then molded with a curing agent, such as benzoyl peroxide, to form heat-resistant silicone products.

In making silicone fluids, it is generally desirable to react cyclic polysiloxane in the above category with hexamethyldisiloxane with a mineral acid so that linear polysiloxanes are formed with chain-stopped trimethylsiloxy units or any other organosiloxy units which it may be desired to insert into the polymer chain.

PRIOR ART

It is known to hydrolyze dimethyldichlorosilane with water in the presence of a cationic surface active agent, where the surface active agent bears a positive charge rather than a negative charge, as is more particularly disclosed in Reedy et al U.S. Pat. No. 3,983,148 issued Sept. 28, 1976. Reedy et al have employed the use of a wide range of cationic surfactants to enhance the yield of the cyclic polysiloxanes, but in their process the cationic surface active agent which is essentially soluble only in the aqueous phase is selected from a limited class of salts or protonated compounds. The use of the sodium lauryl sulfate has an advantage over the Reedy et al surfactant in that the sodium lauryl sulfate is also soluble in the aqueous phase but is much less expensive and more readily available. Furthermore, Reedy et al concentrate on cationic amines which have an undesirable odor while the sodium lauryl sulfate is odor-free. In Reedy et al, the surface active portion of the molecule bears a positive charge, while in my invention the surface active portion bears a negative charge.

The amount of the sodium lauryl sulfate, although it can be varied widely, is used only in small amounts required to effect the desired results of obtaining predominantly large quantities of cyclic polysiloxane where m in formula I is 3-6. Even more advantageous is the fact that in my invention the cyclic polysiloxanes are predominantly of the more desirable tetramer type, that is where m in formula I equals 4, which is the one most employed for making silicone rubbers, fluids, etc.

Thus, the amount of the sulfate which can be employed varies from about 0.05% to about 2%, by weight, based on the weight of the aqueous hydrolysis medium whether water alone or aqueous HCl. Larger amounts than 2% form emulsions causing separation problems. The use of sulfate also permits employing smaller amounts of water for hydrolysis of the dimethyldichlorosilane so that there is less water in the reaction medium and there is the advantage that the formed HCl can usually be removed as gaseous HCl. This is extremely desirable because it reduces the cost of separating the gaseous HCl from the aqueous product. Thus, my invention provides for another method for making cyclic polysiloxanes, predominantly of formula I with relatively small amounts of any higher cyclics.

The amount of water which is used with the dimethyldichlorosilane (molar ratios of from 1 to 4 of water to silane are acceptable) in the practice of my invention is relatively small and should be sufficient to hydrolyze all the silicon-bonded chlorine. Generally, I have found that using about two moles of water per mole of dimethyldichlorosilane is sufficient to yield large amounts of cyclics of formula I. In addition, by following these limitations as far as the amount of water which is used with the dimethyldichlorosilane, there is a direct evolution of HCl resulting in recovery of anhydrous HCl from the hydrolysis reactor.

Generally, greater than one mole water is used per mole of silicon-bonded chlorine, e.g., 1 to 10 moles water per mole silicon-bonded chlorine. If aqueous HCl (e.g., from 5% to saturated HCl) is used to insure the emission of anhydrous HCl, the present invention should follow the proportions recited previously.

The temperature at which the reaction is carried out can be varied within fairly wide limits. Generally, I have found that for liquid phase hydrolysis, temperatures of the order of about 10° to 65° C. are adequate for the purpose and that temperatures higher or lower do not significantly change the results. The mean liquid residence time of the water or the aqueous HCl (if used) and the chlorosilane while hydrolysis reaction is taking place (advantageously with good mixing) is very short and is of the order of about 2-10 minutes, at most. When a 20% aqueous HCl feed stream without the sulfate is used, the hydrolyzate often contains about 38% tetramer and 50% total cyclics. In contrast to this, under similar experimental conditions but with 1%, by weight, sulfate in the aqueous phase, about 59% tetramer and 76% total cyclic polysiloxanes are achieved in the hydrolyzate.

In order that those skilled in the art may better understand how the present invention may be practiced, the following examples are given by way of illustration and not by way of limitation. All parts are by weight, unless otherwise indicated.

Since it is desirable not to have any larger amounts of water in the hydrolysis reaction product than necessary, the water used in hydrolysis is rarely more than 1 to 10 moles water per mole of the chlorosilane and is preferably introduced to the dimethyldichlorosilane as an aqueous HCl solution. The most useful water solution which is presently employed is that where the HCl constitutes about 20%, by weight, of the total weight of the aqueous HCl.

EXAMPLE I

In this example, about 1 mole of dimethyldichlorosilane was fed continuously with stirring into a reactor simultaneously with 2 moles of water, which was in the form of a 20% aqueous HCl solution. The reaction temperature was about 60° C. and the residence time within which the aqueous HCl and the hydrolyzate remained in the reactor was about 5 minutes. After the reaction occurred, the reaction product was continuously removed and then analyzed by gas chromatography. Under these conditions, there was obtained a hydrolyzate, after a phase separation, containing 38% tetramer, 1% trimer, 9% pentamer, and 2% hexamer, or a total cyclic polysiloxane content composed of cyclics of formula I totaling about 50%.

EXAMPLE II

When Example I was repeated but instead a 20 weight percent aqueous HCl solution containing 1%, by weight, sodium lauryl sulfate was added, a significant increase in yields of tetramer and total cyclics resulted. Thus, it was found that the yield of the tetramer has risen to 59%. This process can be carried out under conditions that favor the direct evolution and recovery of anhydrous HCl from the hydrolysis reactor by reducing still further the amount of water which is in the HCl feed used for hydrolysis purposes or increasing the concentration of the aqueous HCl without affecting the yield of cyclics. In this example, there was obtained additionally 15% pentamer, 3% hexamer, and less than 1% trimer, for a total of 78% polycyclosiloxanes.

EXAMPLE III

Using the conditions of Example II, but instead using 0.3%, by weight, sodium lauryl sulfate, the resulting hydrolyzate contained about 1% trimer, 53% tetramer, 13% pentamer, 3% hexamer and about 70% total cyclic polysiloxanes.

It will be course be apparent to those skilled in the art that in addition to the conditions recited in the foregoing example, other conditions, many of which have been described previously, may be employed without departing from the scope of the invention. Thus, the concentration of the sulfate, the temperature of reaction, the ratio of the aqueous HCl hydrolysis feed or water itself may be varied, as may the residence time, the acidity of the HCl feed, etc. within the contemplation of this invention.

What I claim and desire to secure by Letters Patents of the United States is:

1. In a process for preparing cyclic dimethylsiloxanes of the formula:

$([CH_3]_2SiO)_m$ where m predominantly equals a whole number 3–6, by hydrolysis and condensation of dimethyldichlorosilane, the improvement which comprises conducting the reaction in the presence of an effective amount of sodium lauryl sulfate.

2. The process as in claim 1 wherein the temperature of reaction is from about 10°–65° C.

3. The process as in claim 1 wherein the sodium lauryl sulfate is present in an amount ranging from about 0.05 to 2%, by weight, based on the weight of the aqueous feed.

4. The process as in claim 1 wherein the hydrolyzing agent is an aqueous phase containing from 0% HCl to a saturated solution of HCl in water.

5. The process as in claim 1 wherein the water to dimethyldichlorosilane molar ratio is between 1 to 4 moles of the former per mole of the latter.

* * * * *